US009938369B2

(12) United States Patent
Richter et al.

(10) Patent No.: US 9,938,369 B2
(45) Date of Patent: Apr. 10, 2018

(54) USE OF SUCCINONITRILE IN THE PRODUCTION OF POLYISOCYANATES COMPRISING IMINOOXADIAZINEDIONE GROUPS

(71) Applicant: Covestro Deutschland AG, Leverkusen (DE)

(72) Inventors: Frank Richter, Leverkusen (DE); Reinhard Halpasp, Odenthal (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 14/905,853

(22) PCT Filed: Jul. 21, 2014

(86) PCT No.: PCT/EP2014/065575
§ 371 (c)(1),
(2) Date: Jan. 18, 2016

(87) PCT Pub. No.: WO2015/011068
PCT Pub. Date: Jan. 29, 2015

(65) Prior Publication Data
US 2016/0159963 A1  Jun. 9, 2016

(30) Foreign Application Priority Data
Jul. 25, 2013  (EP) .................... 13177980

(51) Int. Cl.
| C08G 18/02 | (2006.01) |
| C07D 273/04 | (2006.01) |
| C08G 18/79 | (2006.01) |
| C08G 18/78 | (2006.01) |
| C08G 18/16 | (2006.01) |

(52) U.S. Cl.
CPC ......... *C08G 18/027* (2013.01); *C07D 273/04* (2013.01); *C08G 18/02* (2013.01); *C08G 18/022* (2013.01); *C08G 18/166* (2013.01); *C08G 18/7887* (2013.01); *C08G 18/79* (2013.01); *C08G 18/792* (2013.01)

(58) Field of Classification Search
CPC .. C08G 18/027; C08G 18/7887; C08G 18/79; C08G 18/792; C08G 18/022; C08G 18/166; C08G 18/02; C07D 273/04
See application file for complete search history.

(56) References Cited

U.S. PATENT DOCUMENTS

| 4,865,795 A | 9/1989 | Shiomura et al. |
| 4,937,339 A | 6/1990 | Shiomura et al. |
| 4,960,848 A | 10/1990 | Scholl et al. |
| 5,013,838 A | 5/1991 | Scholl |
| 5,264,572 A | 11/1993 | Endo et al. |
| 5,914,383 A | 6/1999 | Richter et al. |
| 6,090,939 A | 7/2000 | Richter et al. |
| 6,107,484 A | 8/2000 | Richter et al. |
| 7,595,396 B2 | 9/2009 | Richter |
| 8,058,382 B2 | 11/2011 | Richter et al. |
| 2006/0079694 A1 * | 4/2006 | Richter .................. C08G 18/02 548/227 |
| 2006/0173152 A1 * | 8/2006 | Richter ................ C08G 18/027 528/48 |

FOREIGN PATENT DOCUMENTS

| CA | 2244486 | 10/2007 |
| EP | 0235388 | 9/1987 |

OTHER PUBLICATIONS

Laas, H.J. et al., Synthesis of Aliphatic Polyisocyanates Containing Biuret, Isocyanurate or Uretdione Backbones for Use in Coatings, J. Prakt. Chem., 1994, 36: 185-200 (abstract).
Wendisch, D. et al., Nuclear magnetic resonance contributions to the structure and stereochemistry of ( cyclo) aliphatic isocyanates and their derivatives, Die Angewandte Makromolekulare Chemie, 1986, 141: 173-183 (abstract).

* cited by examiner

*Primary Examiner* — Rabon Sergent
(74) *Attorney, Agent, or Firm* — John E. Mrozinski, Jr.

(57) ABSTRACT

The present invention relates to a method for producing polyisocyanates comprising iminooxadiazinedione groups, wherein at least one monomeric di- and/or tri-isocyanate is oligomerized in the presence of at least one catalyst and succinonitrile. The invention relates further to a reaction system for producing polyisocyanates comprising iminooxadiazinedione groups, and to the use of succinonitrile in the production of polyisocyanates comprising iminooxadiazinedione groups by catalyzed modification of monomeric di- and/or tri-isocyanates.

22 Claims, No Drawings

USE OF SUCCINONITRILE IN THE PRODUCTION OF POLYISOCYANATES COMPRISING IMINOOXADIAZINEDIONE GROUPS

CROSS-REFERENCE TO RELATED APPLICATIONS

This Application is a National Phase Application of PCT/EP2014/065575, filed Jul. 21, 2014, which claims priority to European Application No. 13177980.3, filed Jul. 25, 2013, each of which being incorporated herein by reference.

FIELD OF THE INVENTION

The present invention relates to a method for producing polyisocyanates comprising iminooxadiazinedione groups, wherein at least one monomeric di- and/or tri-isocyanate is oligomerized in the presence of at least one catalyst and succinonitrile. The invention relates further to a reaction system for producing polyisocyanates comprising iminooxadiazinedione groups, and to the use of succinonitrile in the production of polyisocyanates comprising iminooxadiazinedione groups by catalysed modification of monomeric di- and/or tri-isocyanates.

BACKGROUND OF THE INVENTION

The oligo- or poly-merization of isocyanates, here referred to collectively as modification, has been known for a long time. If the modified polyisocyanates comprise free NCO groups, which may also have been temporarily deactivated with blocking agents, they are extraordinarily high-quality starting materials for the production of a large number of polyurethane plastics materials and coating compositions.

A number of industrial processes for modifying isocyanates have become established, wherein the isocyanate to be modified, which in most cases is a diisocyanate, is generally converted by addition of catalysts and then, when the desired degree of conversion of the isocyanate to be modified has been reached, the catalysts are rendered inactive (deactivated or separated off) by suitable measures and the resulting polyisocyanate is generally separated from the unconverted monomer. A summary of these processes of the art is to be found in H. J. Laas et al., *J. Prakt. Chem.* 1994, 336, 185 ff.

A special form of isocyanate modification, which yields products having a high content of iminooxadiazinedione groups (asymmetrical isocyanate trimers) in the products, in addition to the isocyanurate structures (symmetrical isocyanate trimers, frequently referred to hitherto only as "trimers" for the sake of simplicity) which have been known for a long time, is described inter alia in EP 962 455 A1, EP 962 454 A1, EP 896 009 A1, EP 798 299 A1, EP 447 074 A1, EP 379 914 A1, EP 339 396 A1, EP 315 692 A1, EP 295 926 A1 and EP 235 388 A1. (Hydrogen poly)fluorides inter alia have been found to be suitable catalysts therefor.

A disadvantage of the known processes of the art is that the iminooxadiazinedione content in the products is only about 50%, based on the sum of symmetrical (isocyanurate) and asymmetrical trimer (iminooxadiazinedione) and, in the case of higher monomer conversion, on the one hand, and with variations in the reaction temperature, on the other hand, that content decreases further to values below or above an optimum which is to be found in each case.

Although the iminooxadiazinedione content in the products can be influenced in the desired direction by increasing the "HF content" in the catalyst, that is to say by changing from simple fluorides (which generally do not have long-term stability and gradually change to the difluoride form even without the external addition of HF) to difluorides, trifluorides, etc., this procedure has disadvantages (higher HF content in the waste process gas, which must be neutralized in a complex procedure, higher corrosivity of the catalyst solutions, etc.) which do not outweigh the advantages.

SUMMARY OF THE INVENTION

Accordingly, the present invention provides a method for producing polyisocyanates having a high iminooxadiazinedione group content that is not accompanied by the above-mentioned disadvantages: the products exhibit a higher content of iminooxadiazinedione structures than the products that are available by known processes, even without increasing the "HF content" in the catalyst. In addition, the selectivity of the reaction in respect of the iminooxadiazinedione formation is to be less strongly dependent on the reaction temperature.

It is understood that the invention disclosed and described in this specification is not limited to the embodiments summarized in this Summary.

These and other advantages and benefits of the present invention will be apparent from the Detailed Description of the Invention herein below.

DETAILED DESCRIPTION OF THE INVENTION

The present invention will now be described for purposes of illustration and not limitation. Except in the operating examples, or where otherwise indicated, all numbers expressing quantities, percentages, and so forth in the specification are to be understood as being modified in all instances by the term "about."

Any numerical range recited in this specification is intended to include all sub-ranges of the same numerical precision subsumed within the recited range. For example, a range of "1.0 to 10.0" is intended to include all sub-ranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited in this specification is intended to include all lower numerical limitations subsumed therein and any minimum numerical limitation recited in this specification is intended to include all higher numerical limitations subsumed therein. Accordingly, Applicants reserve the right to amend this specification, including the claims, to expressly recite any sub-range subsumed within the ranges expressly recited herein. All such ranges are intended to be inherently described in this specification such that amending to expressly recite any such sub-ranges would comply with the requirements of 35 U.S.C. § 112(a), and 35 U.S.C. § 132(a).

Any patent, publication, or other disclosure material identified herein is incorporated by reference into this specification in its entirety unless otherwise indicated, but only to the extent that the incorporated material does not conflict with existing definitions, statements, or other disclosure material expressly set forth in this specification. As such, and to the extent necessary, the express disclosure as set forth in this specification supersedes any conflicting material incorporated by reference herein. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicants reserve the right to amend this specification to expressly recite any subject matter, or portion thereof, incorporated by reference herein.

Reference throughout this specification to "various non-limiting embodiments," "certain embodiments," or the like, means that a particular feature or characteristic may be included in an embodiment. Thus, use of the phrase "in various non-limiting embodiments," "in certain embodiments," or the like, in this specification does not necessarily refer to a common embodiment, and may refer to different embodiments. Further, the particular features or characteristics may be combined in any suitable manner in one or more embodiments. Thus, the particular features or characteristics illustrated or described in connection with various or certain embodiments may be combined, in whole or in part, with the features or characteristics of one or more other embodiments without limitation. Such modifications and variations are intended to be included within the scope of the present specification.

The grammatical articles "a", "an", and "the", as used herein, are intended to include "at least one" or "one or more", unless otherwise indicated, even if "at least one" or "one or more" is expressly used in certain instances. Thus, these articles are used in this specification to refer to one or more than one (i.e., to "at least one") of the grammatical objects of the article. By way of example, and without limitation, "a component" means one or more components, and thus, possibly, more than one component is contemplated and may be employed or used in an implementation of the described embodiments. Further, the use of a singular noun includes the plural, and the use of a plural noun includes the singular, unless the context of the usage requires otherwise.

The present invention is directed to a method for producing polyisocyanates containing iminooxadiazinedione groups, wherein at least one monomeric di- and/or tri-isocyanate is oligomerized in the presence of at least one catalyst and succinonitrile.

The present invention is based on the finding that the use of succinonitrile as an additive in the catalyzed production of polyisocyanates comprising iminooxadiazinedione groups brings about a significant increase in the iminooxadiazinedione content in the products. The selectivity of the reaction in respect of the iminooxadiazinedione formation is thereby less strongly dependent on the reaction temperature than in the case of the processes known hitherto.

The amount of succinonitrile used can vary within wide limits in the method according to the invention. The amount of succinonitrile used in various embodiments may be from 0.001 to 30%, based on the monomeric di- and/or tri-isocyanate, in other embodiments from 0.001 to 10%, and in yet other embodiments from 0.01 to 5%. As low an amount of additive as possible is of course technically advantageous in order on the one hand to make the space-time yield of polyisocyanate resin high and to keep the catalyst requirement low. However, even with the addition of 5% succinonitrile, the additional amount of catalyst required is still wholly within the technically acceptable range, while the iminooxadiazinedione content in the resulting polyisocyanate resins is significantly increased—and especially does not fall as greatly as without additive even at a higher reaction temperature and with a higher monomer conversion.

By means of the modification method according to the invention, an improved method for producing polyisocyanates having a high content of iminooxadiazinedione groups has therefore been made available in a simple manner.

In one embodiment of the method according to the invention, the succinonitrile to be used is mixed with the monomer(s) to be modified, which is/are optionally dissolved.

The monomers can optionally be dissolved in solvents. Suitable solvents therefor are any chemicals that do not enter into a reaction that interferes with the conversion according to the invention with succinonitrile, with the catalysts used and/or with the monomers used. Examples which may be mentioned are: optionally branched or cyclic aliphatic hydrocarbons or hydrocarbon mixtures having a molar weight of up to approximately 300 g/mol, optionally halogenated, aromatic hydrocarbons or hydrocarbon mixtures having a molar weight of up to 350 g/mol, aliphatic or aromatic ethers, esters or carbonates having a molar weight of up to 350 g/mol and the like.

In a further embodiment, the succinonitrile to be used is added to the catalyst or the catalyst solution.

Suitable catalysts are in principle any compounds known in the art which have previously been described for this purpose, as such or in solution. Particularly suitable are substances having a salt-like structure with cations which ensure good solubility in the isocyanate medium, in particular tetraorganyl-ammonium salts and -phosphonium salts, with anions selected from the group $RfCR_1R_2COOH$, wherein Rf represents a straight-chained or branched perfluoroalkyl radical and $R_1$ and $R_2$ independently of one another represent H or straight-chained or branched organyl radicals, fluoride ($F^-$), di- and/or poly-(hydrogen) fluorides ($[F^-\times HF)_m]$), wherein m has a numerical value in some embodiments of from 0.001 to 20, in other embodiments of from 0.1 to 20, in still other embodiments of from 0.5 to 20, and in yet other embodiments of from 0.5 to 5.

The di- and/or poly-(hydrogen) fluoride ($[F^-\times HF)_m]$) can in particular embodiments be a quaternary ammonium fluoride, ammonium difluoride, ammonium trifluoride, a higher ammonium polyfluoride, a phosphonium fluoride, a phosphonium difluoride, a phosphonium trifluoride and/or a higher phosphonium polyfluoride, preferably those which can be prepared by mixing quaternary ammonium and phosphonium fluorides or hydroxides with corresponding amounts of hydrogen fluoride, optionally pre-dissolved in alcohols or water.

Suitable solvents for the catalyst(s) are any compounds which do not react with the catalyst and are capable of dissolving it to a sufficient degree. For the above-mentioned tetraorganyl-ammonium salts and phosphonium salts, for example, they are aliphatic or aromatic hydrocarbons, alcohols, esters and ethers. Alcohols are preferably used.

The amount of catalyst required in the method according to the invention does not differ significantly from that observed in the bulk modification of the known art. The catalyst can be used, for example, in an amount of from 1 mol-ppm to 1 mol-%, preferably from 5 mol-ppm to 0.1 mol-%, based on the amount of monomer.

Any known isocyanates can in principle be used within the scope of the method according to the invention. Di- and/or tri-isocyanates having aliphatically, cycloaliphatically, aralphatically and/or aromatically bonded isocyanate groups are preferably used, individually or in arbitrary mixtures with one another. The methods by which the above-mentioned (poly)isocyanates are generated, that is to say with or without the use of phosgene, are unimportant. Particular mention may be made of: hexamethylene diisocyanate (HDI), 2-methylpentane 1,5-diisocyanate, 2,4,4-trimethyl-1,6-hexane diisocyanate, 2,2,4-trimethyl-1,6-hexane diisocyanate, 4-isocyanatomethyl-1,8-octane diisocyanate, 3(4)-isocyanatomethyl-1-methylcyclohexyl isocyanate (IMCI), isophorone diisocyanate (IPDI), 1,3- and 1,4-bis(isocyanatomethyl)benzene (XDI), 1,3- and 1,4-bis (isocyanatomethyl)cyclohexane (H6XDI), 2,4- and 2,6-toluylene diisocyanate (TDI), bis(4-isocyanatophenyl)methane (4,4'MDI), 4-isocyanatophenyl-2-isocyanatophenylmethane (2,4'MDI) and also polynuclear products which are obtainable by formaldehyde-aniline polycondensation and subsequent conversion of the resulting (poly)amines into the corresponding (poly)isocyanates (polymeric MDI). Aliphatic di- and/or tri-isocyanates are preferably used, particularly preferably aliphatic diisocyanates. Most particular preference is given to the use of hexamethylene diisocyanate (HDI), 2-methylpentane 1,5-diisocyanate, 2,4,4-trimethyl-1,6-hexane diisocyanate, 2,2,4-trimethyl-1,6-hexane diisocyanate and/or 4-isocyanatomethyl-1,8-octane diisocyanate, yet further preference being given to HDI.

The method according to various embodiments of the invention can be carried out, for example, in the temperature range of from 0° C. to +250° C., in other embodiments from 20 to 180° C., in yet other embodiments from 40 to 150° C., and in still other embodiments from 50 to 90° C.

In a further embodiment of the method according to the invention, the oligomerization can be terminated when from 5 to 80 wt. %, preferably from 10 to 60 wt. %, of the monomeric di- and/or tri-isocyanate used have been converted. The oligomerization can be terminated, for example, by deactivating the catalyst. A large number of described methods of the art are suitable in principle for deactivating the catalyst, such as, for example, the addition of (sub- or super-)stoichiometric amounts of acids or acid derivatives (e.g. benzoyl chloride, acid esters of acids containing phosphorus or sulfur, those acids themselves, etc., but not HF), adsorptive binding of the catalyst and subsequent separation by filtration, or combinations thereof.

After deactivation of the catalyst, the unconverted monomer and any solvent used concomitantly can be separated off by any known separation techniques such as, for example, distillation, optionally in the special form of thin-film distillation, extraction or crystallization/filtration. Combinations of two or more of these techniques can of course also be used.

If the polyisocyanate produced according to the invention is to comprise free, unconverted monomer, as is of interest, for example, for further processing to NCO-blocked products, separation of the monomer after deactivation of the catalyst can be omitted.

The unconverted monomer is separated off in certain embodiments by distillation. The products according to the invention in some embodiments have a residual monomer content, after separation, of <0.5 wt. %, in other embodiments <0.25 wt. %, in yet other embodiments <0.1 wt. %.

Compared with catalysis by means of, for example, quaternary phosphonium salts without the use of additives (bulk modification, see Comparative Example 1), a significant increase in the iminooxadiazinedione content in the products is observed in the method according to the invention, in particular at a higher monomer conversion, under otherwise identical reaction conditions.

According to a further, continuous embodiment of the method according to the invention, the oligomerization can be carried out in a tubular reactor. This is advantageous because the catalysts according to the invention hereby have a significantly lower tendency spontaneously to form gel particles in the product as compared with the known catalysts of the art, even when used in a highly concentrated solution or in the form of the pure active substance.

The present invention relates further to embodiments of a reaction system for producing polyisocyanates comprising iminooxadiazinedione groups, which reaction system comprises at least one monomeric di- and/or tri-isocyanate as well as at least one catalyst and succinonitrile.

The present invention further provides embodiments for the use of succinonitrile in the production of polyisocyanates comprising iminooxadiazinedione groups by catalyzed modification of monomeric di- and/or tri-isocyanates.

The products or product mixtures obtainable by the method according to various embodiments of the invention are therefore starting materials which can be used in a versatile manner for producing optionally foamed plastics material(s) as well as coatings, coating compositions, adhesives and aggregates. They are suitable, optionally in NCO-blocked form, in particular for producing optionally water-dispersible one- and two-component polyurethane coatings, on account of their reduced solution and melt viscosity, as compared with products based (predominantly) on isocyanurate polyisocyanate, with an otherwise equally high or improved property profile. The HDI-based products according to the invention, even when highly diluted in coating solvents, are thus more stable to the occurrence of flocculation or turbidity than corresponding isocyanurate-based products.

They can be used in pure form or in conjunction with other isocyanate derivatives of the art, such as, for example, polyisocyanates comprising uretdione, biuret, allophanate, isocyanurate and/or urethane groups, the free NCO groups of which have optionally been deactivated with blocking agents.

EXAMPLES

The present invention is explained in greater detail below by means of examples.

All amounts are by mass, unless indicated otherwise.

The NCO content of the resins described in the examples and comparative examples was determined by titration according to DIN 53 185.

The refractive index nD20 was determined as the critical angle of total internal reflection of the light of the wavelength of the D-line in the Na emission spectrum (589 nm). The measuring instrument used was an "Automatic Refractometer GPR 11-37" from Index Instruments.

Mol-% data were determined by NMR spectroscopy and, unless indicated otherwise, always relate to the sum of the NCO secondary products. The measurements were carried out using DPX 400 or DRX 700 instruments from Brucker on approximately 5% (1H-NMR) or approximately 50% (13C-NMR) samples in dry C6D6 at a frequency of 400 or 700 MHz (1H-NMR) or 100 or 176 MHz (13C-NMR). As reference for the ppm scale, there were used small amounts of tetramethylsilane in the solvent with 0 ppm 1H-NMR chem. shift. Alternatively, the signal of the $C_6D_5H$ contained in the solvent was used as reference: 7.15 ppm $^1$H-NMR chem. shift, 128.02 ppm $^{13}$C-NMR chem. shift. Data for the chemical shift of the compounds in question were taken from the literature (see D. Wendisch, H. Reiff and D. Dieterich, Die Angewandte Makromolekulare Chemie 141, 1986, 173-183 and literature cited therein, as well as EP-A 896 009).

The residual monomer contents were determined by gas chromatography.

Unless indicated otherwise, all the reactions were carried out under a nitrogen atmosphere.

The diisocyanates used are products of Covestro Deutschland AG; all other commercially available chemicals were obtained from Aldrich. The preparation of the hydrogen polyfluoride catalysts is known in the literature and is described inter alia in EP 962 454.

Example 1—Comparative Example 1000 g of HDI were placed in a double-walled flat ground flange vessel adjusted to 40° C. by an external circuit and having a stirrer, a reflux condenser connected to an inert gas system (nitrogen/vacuum) and a thermometer, and freed of dissolved gases by stirring for one hour in vacuo (0.1 mbar). After aeration with nitrogen, the refractive index at the frequency of the light of the D-line of the Na emission spectrum was measured at 20° C. ($n_D^{20}$ hereinbelow), heating to the minimum temperature indicated in Table 1 was carried out, and then the amount of catalyst indicated in Table 1 (based on the mass of HDI used, in the form of a 70% solution in isopropanol) was metered in, in portions, in such a manner that the internal temperature did not exceed the maximum value indicated in Table 1. When about 1 mol. of NCO groups had been converted, the catalyst was deactivated by addition of an amount of p-toluenesulfonic acid (in the form of a 40% solution in isopropanol) equivalent to the catalyst, and the mixture was then stirred for a further 30 minutes at reaction temperature and subsequently worked up.

Working up of the crude solution, the $n_D^{20}$ of which was 1.4618 in the first pass (Example 1-A), was carried out by vacuum distillation in a thin-film evaporator, short path evaporator (SPE) type, with an upstream pre-evaporator (PE) (distillation conditions: pressure: 0.08+/−0.04 mbar, PE temperature: 120° C., SPE temp.: 140° C.), unconverted monomer being separated off as the distillate and the low-monomer polyisocyanate resin being separated off as the bottom product (initial pass: Example 1-A). The polyisocyanate resin was separated off and the distillate was collected in a second flat ground flange stirring apparatus, of identical construction to the first, and made up to the starting amount (1000 g) with freshly degassed HDI. The procedure was then as described at the beginning, with the difference that the isocyanate conversion (indicated by the refractive index of the raw materials) and/or the reaction temperature was raised stepwise from pass to pass. This procedure was repeated several times. The results are found in Table 1.

TABLE 1

| Ex. 1- | Reaction temperature (min-max) [° C.] | $Bu_4P^+$ $[HF_2]^-$ solution[a] [g] | Delta-$n_D^{20}$ [b] | Amount of resin [g] | Resin NCO content [%] | Iminooxa-diazinediones[c] | Isocyan-urates[c] | Uretdiones[c] |
|---|---|---|---|---|---|---|---|---|
| A | 40-42 | 0.83 | 0.0093 | 191 | 23.6 | 41.0% | 57.9% | 1.1% |
| B | 60-62 | 0.35 | 0.0081 | 207 | 23.0 | 44.0% | 53.0% | 3.0% |
| C | 80-84 | 0.49 | 0.0075 | 156 | 23.9 | 27.0% | 67.5% | 5.5% |
| D | 100-105 | 1.14 | 0.0065 | 165 | 23.8 | 26.2% | 57.9% | 15.9% |
| E | 60-62 | 0.40 | 0.0122 | 251 | 23.7 | 43.0% | 51.0% | 6.0% |
| F | 80-81 | 0.36 | 0.0135 | 252 | 23.1 | 31.3% | 58.9% | 9.8% |
| G | 100-105 | 1.86 | 0.0134 | 284 | 22.8 | 23.4% | 69.2% | 7.4% |
| H | 60-62 | 0.71 | 0.0191 | 385 | 22.4 | 42.9% | 53.9% | 3.2% |
| I | 80-81 | 0.78 | 0.0189 | 358 | 22.3 | 28.9% | 63.7% | 7.4% |
| J | 100-105 | 5.20 | 0.0176 | 398 | 22.0 | 14.4% | 71.0% | 14.6% |
| K | 60-62 | 0.80 | 0.028 | 535 | 21.0 | 38.2% | 58.3% | 3.5% |
| L | 80-81 | 1.07 | 0.0292 | 508 | 20.8 | 24.4% | 70.8% | 4.7% |
| M | 60-62 | 1.12 | 0.0327 | 608 | 20.5 | 37.7% | 60.0% | 2.3% |
| N | 60-62 | 1.18 | 0.0395 | 696 | 19.2 | 32.5% | 65.8% | 1.7% |
| O | 60-62 | 1.20 | 0.0484 | 804 | 17.5 | 32.0% | 65.7% | 2.3% |

[a] 70% in iPrOH;
[b] Refractive index of the reaction mixture after action of the stopper before distillation-starting value before catalyst addition,
[c] mol-% acc. to NMR, based on the sum of the stated 3 NCO secondary products formed in the modification reaction, not taken into consideration: urethanes/allophanates from the reaction of the catalyst solvent with the isocyanate Example 2—According to the Invention Additive: 5% Succinonitrile The procedure was as described in Example 1, with the difference that 5% succinonitrile was added once to the degassed HDI before the first reaction (Example 2-A). The reaction temperature was between 60 and 62° C. The results are found in Table 2.

TABLE 2

| Ex. 2 | Bu$_4$P$^+$[HF$_2$]$^-$ solution[a] [g] | Delta-n$_D$[b] | Amount of resin [g] | Resin-NCO [%] | Iminooxa-diazinediones[c] | Iso-cyanurates[c] | Uret-diones[c] |
|---|---|---|---|---|---|---|---|
| A | 1.83 | 0.0070 | 180 | 23.4 | 67.0% | 29.1% | 3.9% |
| B | 1.83 | 0.0064 | 173 | 23.4 | 63.8% | 31.9% | 4.3% |
| C | 1.84 | 0.0069 | 169 | 23.3 | 60.6% | 35.4% | 4.0% |
| D | 1.88 | 0.0072 | 172 | 23.3 | 62.1% | 33.9% | 4.0% |
| E | 2.06 | 0.0069 | 171 | 23.3 | 61.5% | 34.4% | 4.1% |

[a]-[c] see footnotes to Table 1

Example 3—According to the Invention

Additive: 1% Succinonitrile, Variation of the Reaction Temperature and of the Conversion The procedure was as described in Example 1, with the difference that 1% succinonitrile was added once to the degassed HDI before the first reaction (Example 3-A). The further reaction parameters and results are found in Table 3.

TABLE 3

| Ex. 3- | Reaction temperature [° C.], +/−0.5° C. | Bu$_4$P$^+$[HF$_2$]$^-$ solution[a] [g] | Delta-n$_D^{20}$[c] | Amount of resin [g] | Resin NCO content [%] | Iminooxa-diazinediones[d] | Iso-cyanurates[d] | Uretdiones[d] |
|---|---|---|---|---|---|---|---|---|
| A | 60 | 1.77 | 0.0090 | 174 | 23.5 | 62.1% | 33.8% | 4.1% |
| B | 60 | 1.49 | 0.0100 | 194 | 23.5 | 63.6% | 32.7% | 3.8% |
| C | 60 | 1.40 | 0.0100 | 198 | 23.6 | 64.2% | 31.7% | 4.1% |
| D | 40 | 0.83 | 0.0095 | 191 | 23.6 | 47.6% | 50.8% | 1.6% |
| E | 80 | 2.03 | 0.0088 | 169 | 23.4 | 55.2% | 35.7% | 9.1% |
| F | 100 | 2.80 | 0.0084 | 171 | 23.2 | 36.9% | 45.7% | 17.3% |
| G | 60 | 1.21 | 0.0135 | 274 | 22.8 | 60.1% | 36.1% | 3.8% |
| H | 80 | 2.50 | 0.0131 | 265 | 23.0 | 52.7% | 38.6% | 8.7% |
| I | 60 | 2.41 | 0.0203 | 384 | 22.3 | 61.9% | 34.3% | 3.8% |
| J | 80 | 2.78 | 0.0191 | 364 | 22.1 | 48.4% | 44.7% | 6.9% |
| K | 60 | 2.57 | 0.0237 | 515 | 20.9 | 60.5% | 36.5% | 3.0% |
| L | 80 | 4.09 | 0.0294 | 493 | 20.8 | 44.9% | 50.2% | 4.9% |

[a]-[c] see footnotes to Table 1

As is apparent from a comparison of the corresponding experiments from Comparative Example 1 and the results listed in Table 3, the addition of succinonitrile has a positive effect with regard to the maintenance of as high an iminooxadiazinedione group content in the products as possible both when the monomer conversion is increased (higher amount of resin) and when the reaction temperature is increased.

Example 4—According to the Invention

Catalyst Solution with Additive

The procedure was as described in Example 1, with the difference that 12.3% succinonitrile was added to the catalyst solution in the first 6 tests of the series (approximately equimolar based on catalyst). The reaction temperature was between 60 and 65° C. The results are found in Table 4.

TABLE 4

| Ex. 4 | Bu$_4$P$^+$[HF$_2$]$^-$ solution[a] [g] | Delta-n$_D$[b] | Amount of resin [g] | Resin-NCO [%] | Iminooxa-diazinediones[c] | Iso-cyanurates[c] | Uretdiones[c] |
|---|---|---|---|---|---|---|---|
| A | 0.79 | 0.0090 | 176 | 23.7 | 49.0% | 46.5% | 4.5% |
| B | 0.69 | 0.0078 | 175 | 23.4 | 47.6% | 49.0% | 3.4% |
| C | 0.73 | 0.0110 | 216 | 23.6 | 53.5% | 41.6% | 4.9% |
| D | 0.66 | 0.0078 | 170 | 23.7 | 56.7% | 38.7% | 4.5% |
| E | 0.53 | 0.0077 | 172 | 23.3 | 59.8% | 36.5% | 3.6% |
| F | 0.63 | 0.0074 | 172 | 23.6 | 58.4% | 36.6% | 5.0% |
| G | 0.69 | 0.0090 | 174 | 23.7 | 57.4% | 37.2% | 5.5% |
| H | 0.56 | 0.0085 | 174 | 23.6 | 56.1% | 38.7% | 5.2% |
| I | 0.51 | 0.0074 | 162 | 23.4 | 58.0% | 37.0% | 5.0% |
| J | 0.53 | 0.0076 | 170 | 23.6 | 58.1% | 37.1% | 4.8% |
| K | 0.54 | 0.0082 | 172 | 23.5 | 58.1% | 37.1% | 4.7% |

[a] to test 4-F approx. 60% in iPrOH, comprises 12.3% succinonitrile, from test 4-G 70% in iPrOH;
[b]-[c] see footnotes to Table 1

The results show that the use of succinonitrile as an additive in the catalysed production of polyisocyanates comprising iminooxadiazinedione groups brings about a significant increase in the iminooxadiazinedione content in the products. In addition, the examples show that the selectivity of the reaction in respect of the iminooxadiazinedione formation is less strongly dependent on the reaction temperature than in the case of the processes known hitherto.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth herein. Such embodiments may be obtained, for example, by combining, modifying, or reorganizing any of the disclosed steps, components, elements, features, aspects, characteristics, limitations, and the like, of the various non-limiting embodiments described in this specification. In this manner, Applicant(s) reserve the right to amend the claims during prosecution to add features as variously described in this specification, and such amendments comply with the requirements of 35 U.S.C. § 112(a), and 35 U.S.C. § 132(a).

Various aspects of the subject matter described herein are set out in the following numbered clauses:

1. Method for producing polyisocyanates comprising iminooxadiazinedione groups, wherein at least one monomeric di- and/or tri-isocyanate is oligomerised in the presence of at least one catalyst and succinonitrile.

2. Method according to clause 1, characterised in that the amount of succinonitrile used is from 0.001 to 30%, based on the monomeric di- and/or tri-isocyanate, in particular from 0.001 to 10%, preferably from 0.01 to 5%.

3. Method according to clause 1 or 2, characterised in that there is used as the monomeric di- and/or tri-isocyanate an aliphatic diisocyanate, in particular hexamethylene diisocyanate (HDI), 2-methylpentane 1,5-diisocyanate, 2,4,4-trimethyl-1,6-hexane diisocyanate, 2,2,4-trimethyl-1,6-hexane diisocyanate and/or 4-isocyanatomethyl-1,8-octane diisocyanate, preferably HDI.

4. Method according to any one of the preceding clauses, characterised in that there is used as the catalyst a tetraorganyl-ammonium salt and/or—phosphonium salt, wherein the anions of the tetraorganyl-ammonium salt and/or—phosphonium salt are selected in particular from the group: $RfCR_1R_2COO^-$, wherein Rf represents a straight-chained or branched perfluoroalkyl radical and $R_1$ and $R_2$ independently of one another represent H, straight-chained or branched organyl radicals, fluoride ($F^-$), di- and/or poly-(hydrogen) fluorides ($[F^- \times HF]_m$), wherein m has a numerical value of from 0.001 to 20, preferably from 0.1 to 20, particularly preferably from 0.5 to 20, most particularly preferably from 0.5 to 5.

5. Method according to clause 4, characterised in that the di- and/or poly-(hydrogen) fluoride ($[F^- \times HF]_m$) is a quaternary ammonium fluoride, ammonium difluoride, ammonium trifluoride, a higher ammonium polyfluoride, a phosphonium fluoride, a phosphonium difluoride, a phosphonium trifluoride and/or a higher phosphonium polyfluoride, preferably those which can be prepared by mixing quaternary ammonium and phosphonium fluorides or hydroxides with corresponding amounts of hydrogen fluoride, optionally pre-dissolved in alcohols or water.

6. Method according to any one of the preceding clauses, characterised in that the catalyst/catalyst mixture is used in an amount of from 1 mol-ppm to 1 mol-%, preferably from 5 mol-ppm to 0.1 mol-%, in each case based on the amount of monomeric di- and/or tri-isocyanate.

7. Method according to any one of the preceding clauses, characterised in that the method is carried out in the temperature range of from 0° C. to +250° C., in particular from 20 to 180° C., preferably from 40 to 150° C., particularly preferably from 50 to 90° C.

8. Method according to any one of the preceding clauses, characterised in that the oligomerisation is terminated when from 5 to 80 wt. %, preferably from 10 to 60 wt. %, of the monomeric di- and/or tri-isocyanate used has been converted.

9. Method according to clause 8, characterised in that the oligomerisation is terminated by deactivation of the catalyst, in particular by addition of an acid or of an acid derivative such as benzoyl chloride, an acid ester of acids containing phosphorus or sulfur, those acids themselves, adsorptive binding of the catalyst and subsequent separation by filtration, or combinations thereof.

10. Method according to clause 8 or 9, characterised in that unconverted monomer is separated from the reaction mixture.

11. Polyisocyanates comprising iminooxadiazinedione groups, which can be prepared by a method according to any one of clauses 1 to 10.

12. Reaction system for producing polyisocyanates comprising iminooxadiazinedione groups, which reaction system comprises at least one monomeric di- and/or tri-isocyanate as well as at least one catalyst and succinonitrile.

13. Use of succinonitrile in the production of polyisocyanates comprising iminooxadiazinedione groups by catalysed modification of monomeric di- and/or tri-isocyanates.

The Use of Succinonitrile in the Production of Polyisocyanates Comprising Iminooxadiazinedione Groups The present invention relates to a method for producing polyisocyanates comprising iminooxadiazinedione groups, wherein at least one monomeric di- and/or tri-isocyanate is oligomerised in the presence of at least one catalyst and succinonitrile. The invention relates further to a reaction system for producing polyisocyanates comprising iminooxadiazinedione groups, and to the use of succinonitrile in the production of polyisocyanates comprising iminooxadiazinedione groups by catalysed modification of monomeric di- and/or tri-isocyanates.

The oligo- or poly-merisation of isocyanates, here referred to collectively as modification, has been known for a long time. If the modified polyisocyanates comprise free NCO groups, which may also have been temporarily deactivated with blocking agents, they are extraordinarily high-quality starting materials for the production of a large number of polyurethane plastics materials and coating compositions.

A number of industrial processes for modifying isocyanates have become established, wherein the isocyanate to be modified, which in most cases is a diisocyanate, is generally converted by addition of catalysts and then, when the desired degree of conversion of the isocyanate to be modified has been reached, the catalysts are rendered inactive (deactivated or separated off) by suitable measures and the resulting polyisocyanate is generally separated from the unconverted monomer. A summary of these processes of the prior art is to be found in H. J. Laas et al., *J. Prakt. Chem.* 1994, 336, 185 ff.

A special form of isocyanate modification, which yields products having a high content of iminooxadiazinedione groups (asymmetrical isocyanate trimers) in the products, in addition to the isocyanurate structures (symmetrical isocyanate trimers, frequently referred to hitherto only as "trimers" for the sake of simplicity) which have been known for a long time, is described inter alia in EP 962 455 A1, EP 962 454 A1, EP 896 009 A1, EP 798 299 A1, EP 447 074 A1, EP 379 914 A1, EP 339 396 A1, EP 315 692 A1, EP 295 926 A1 and EP 235 388 A1. (Hydrogen poly)fluorides inter alia have been found to be suitable catalysts therefor.

A disadvantage of the known processes of the prior art is that the iminooxadiazinedione content in the products is only about 50%, based on the sum of symmetrical (isocyanurate) and asymmetrical trimer (iminooxadiazinedione) and, in the case of higher monomer conversion, on the one hand, and with variations in the reaction temperature, on the other hand, that content decreases further to values below or above an optimum which is to be found in each case.

Although the iminooxadiazinedione content in the products can be influenced in the desired direction by increasing the "HF content" in the catalyst, that is to say by changing from simple fluorides (which generally do not have long-term stability and gradually change to the difluoride form even without the external addition of HF) to difluorides, trifluorides, etc., this procedure has disadvantages (higher HF content in the waste process gas, which must be neutralised in a complex procedure, higher corrosivity of the catalyst solutions, etc.) which do not outweigh the advantages.

Accordingly, the object underlying the invention was to provide a method for producing polyisocyanates having a high iminooxadiazinedione group content that is not accompanied by the above-mentioned disadvantages: the products are to exhibit a higher content of iminooxadiazinedione structures than the products that are available by known processes of the prior art, even without increasing the "HF content" in the catalyst. In addition, the selectivity of the reaction in respect of the iminooxadiazinedione formation is to be less strongly dependent on the reaction temperature.

The object is achieved by a method for producing polyisocyanates comprising iminooxadiazinedione groups, wherein at least one monomeric di- and/or tri-isocyanate is oligomerised in the presence of at least one catalyst and succinonitrile.

The present invention is based on the finding that the use of succinonitrile as an additive in the catalysed production of polyisocyanates comprising iminooxadiazinedione groups brings about a significant increase in the iminooxadiazinedione content in the products. The selectivity of the reaction in respect of the iminooxadiazinedione formation is thereby less strongly dependent on the reaction temperature than in the case of the processes known hitherto.

The amount of succinonitrile used can vary within wide limits in the method according to the invention. The amount of succinonitrile used is preferably from 0.001 to 30%, based on the monomeric di- and/or tri-isocyanate, particularly preferably from 0.001 to 10%, most particularly preferably from 0.01 to 5%. As low an amount of additive as possible is of course technically advantageous in order on the one hand to make the space-time yield of polyisocyanate resin high and to keep the catalyst requirement low. However, even with the addition of 5% succinonitrile, the additional amount of catalyst required is still wholly within the technically acceptable range, while the iminooxadiazinedione content in the resulting polyisocyanate resins is significantly increased and especially does not fall as greatly as without additive even at a higher reaction temperature and with a higher monomer conversion.

By means of the modification method according to the invention, an improved method for producing polyisocyanates having a high content of iminooxadiazinedione groups has therefore been made available in a simple manner.

In one embodiment of the method according to the invention, the succinonitrile to be used is mixed with the monomer(s) to be modified, which is/are optionally dissolved.

The monomers can optionally be dissolved in solvents. Suitable solvents therefor are any chemical individuals that do not enter into a reaction that interferes with the conversion according to the invention with succinonitrile, with the catalysts used and/or with the monomers used. Examples which may be mentioned are: optionally branched or cyclic aliphatic hydrocarbons or hydrocarbon mixtures having a molar weight of up to approximately 300 g/mol, optionally halogenated, aromatic hydrocarbons or hydrocarbon mixtures having a molar weight of up to 350 g/mol, aliphatic or aromatic ethers, esters or carbonates having a molar weight of up to 350 g/mol and the like.

In a further embodiment, the succinonitrile to be used is added to the catalyst or the catalyst solution.

Suitable catalysts are in principle any compounds of the prior art which have previously been described for this purpose, as such or in solution. Particularly suitable are substances having a salt-like structure with cations which ensure good solubility in the isocyanate medium, in particular tetraorganyl-ammonium salts and -phosphonium salts, with anions selected from the group $RfCR_1R_2COOH$, wherein Rf represents a straight-chained or branched perfluoroalkyl radical and $R_1$ and $R_2$ independently of one another represent H or straight-chained or branched organyl radicals, fluoride ($F^-$), di- and/or poly-(hydrogen) fluorides ($[F^- \times HF)_m]$), wherein m has a numerical value of from 0.001 to 20, preferably from 0.1 to 20, particularly preferably from 0.5 to 20, most particularly preferably from 0.5 to 5.

The di- and/or poly-(hydrogen) fluoride ($[F^- \times HF)_m]$) can in particular be a quaternary ammonium fluoride, ammonium difluoride, ammonium trifluoride, a higher ammonium polyfluoride, a phosphonium fluoride, a phosphonium difluoride, a phosphonium trifluoride and/or a higher phosphonium polyfluoride, preferably those which can be prepared by mixing quaternary ammonium and phosphonium fluorides or hydroxides with corresponding amounts of hydrogen fluoride, optionally pre-dissolved in alcohols or water.

Suitable solvents for the catalyst(s) are any compounds which do not react with the catalyst and are capable of dissolving it to a sufficient degree. For the above-mentioned tetraorganyl-ammonium salts and -phosponium salts, for example, they are aliphatic or aromatic hydrocarbons, alcohols, esters and ethers. Alcohols are preferably used.

The amount of catalyst required in the method according to the invention does not differ significantly from that observed in the bulk modification of the prior art. The catalyst can be used, for example, in an amount of from 1 mol-ppm to 1 mol-%, preferably from 5 mol-ppm to 0.1 mol-%, based on the amount of monomer.

Any known isocyanates can in principle be used within the scope of the method according to the invention. Di- and/or tri-isocyanates having aliphatically, cycloaliphatically, araliphatically and/or aromatically bonded isocyanate groups are preferably used, individually or in arbitrary mixtures with one another. The methods by which the above-mentioned (poly)isocyanates are generated, that is to say with or without the use of phosgene, are unimportant. Particular mention may be made of: hexamethylene diisocyanate (HDI), 2-methylpentane 1,5-diisocyanate, 2,4,4-trimethyl-1,6-hexane diisocyanate, 2,2,4-trimethyl-1,6-hexane diisocyanate, 4-isocyanatomethyl-1,8-octane diisocyanate, 3(4)-isocyanatomethyl-1-methylcyclohexyl isocyanate (IMCI), isophorone diisocyanate (IPDI), 1,3- and 1,4-bis(isocyanatomethyl)benzene (XDI), 1,3- and 1,4-bis(isocyanatomethyl)cyclohexane (H6XDI), 2,4- and 2,6-toluylene diisocyanate (TDI), bis(4-isocyanatophenyl)methane (4,4'MDI), 4-isocyanatophenyl-2-isocyanatophenylmethane (2,4'MDI) and also polynuclear products which are obtainable by formaldehyde-aniline polycondensation and subsequent conversion of the resulting (poly)amines into the corresponding (poly)isocyanates (polymeric MDI). Aliphatic di- and/or tri-isocyanates are preferably used, particularly preferably aliphatic diisocyanates. Most particular preference is given to the use of hexamethylene diisocyanate (HDI), 2-methylpentane 1,5-diisocyanate, 2,4,4-trimethyl-1,6-hexane diisocyanate, 2,2,4-trimethyl-1,6-hexane diisocyanate and/or 4-isocyanatomethyl-1,8-octane diisocyanate, yet further preference being given to HDI.

The method according to the invention can be carried out, for example, in the temperature range of from 0° C. to +250° C., in particular from 20 to 180° C., preferably from 40 to 150° C., particularly preferably from 50 to 90° C.

In a further form of the method according to the invention, the oligomerisation can be terminated when from 5 to 80 wt. %, preferably from 10 to 60 wt. %, of the monomeric di- and/or tri-isocyanate used have been converted. The oligomerisation can be terminated, for example, by deactivating the catalyst. A large number of prior-described methods of the prior art are suitable in principle for deactivating the catalyst, such as, for example, the addition of (sub- or super-) stoichiometric amounts of acids or acid derivatives (e.g. benzoyl chloride, acid esters of acids containing phosphorus or sulfur, those acids themselves, etc., but not HF), adsorptive binding of the catalyst and subsequent separation by filtration, or combinations thereof.

After deactivation of the catalyst, the unconverted monomer and any solvent used concomitantly can be separated off by any known separation techniques such as, for example, distillation, optionally in the special form of thin-film distillation, extraction or crystallisation/filtration. Combinations of two or more of these techniques can of course also be used.

If the polyisocyanate produced according to the invention is to comprise free, unconverted monomer, as is of interest, for example, for further processing to NCO-blocked products, separation of the monomer after deactivation of the catalyst can be omitted.

The unconverted monomer is preferably separated off, in particular by distillation. The products according to the invention preferably have a residual monomer content, after separation, of <0.5 wt. %, preferably <0.25 wt. %, particularly preferably <0.1 wt. %.

Compared with catalysis by means of, for example, quaternary phosphonium salts without the use of additives (bulk modification, see comparative example 1), a significant increase in the iminooxadiazinedione content in the products is observed in the method according to the invention, in particular at a higher monomer conversion, under otherwise identical reaction conditions.

According to a further preferred, continuous embodiment of the method according to the invention, the oligomerisation can be carried out in a tubular reactor. This is advantageous because the catalysts according to the invention hereby have a significantly lower tendency spontaneously to form gel particles in the product as compared with the known catalysts of the prior art, even when used in a highly concentrated solution or in the form of the pure active substance.

The present invention relates further to a reaction system for producing polyisocyanates comprising iminooxadiazinedione groups, which reaction system comprises at least one monomeric di- and/or tri-isocyanate as well as at least one catalyst and succinonitrile.

The present invention further provides the use of succinonitrile in the production of polyisocyanates comprising iminooxadiazinedione groups by catalysed modification of monomeric di- and/or tri-isocyanates.

The products or product mixtures obtainable by the method according to the invention are therefore starting materials which can be used in a versatile manner for producing optionally foamed plastics material(s) as well as coatings, coating compositions, adhesives and aggregates. They are suitable, optionally in NCO-blocked form, in particular for producing optionally water-dispersible one- and two-component polyurethane coatings, on account of their reduced solution and melt viscosity, as compared with products based (predominantly) on isocyanurate polyisocyanate, with an otherwise equally high or improved property profile. The HDI-based products according to the invention, even when highly diluted in coating solvents, are thus more stable to the occurrence of flocculation or turbidity than corresponding isocyanurate-based products.

They can be used in pure form or in conjunction with other isocyanate derivatives of the prior art, such as, for example, polyisocyanates comprising uretdione, biuret, allophanate, isocyanurate and/or urethane groups, the free NCO groups of which have optionally been deactivated with blocking agents.

EXAMPLES

The present invention is explained in greater detail below by means of examples.

All amounts are by mass, unless indicated otherwise.

The NCO content of the resins described in the examples and comparative examples was determined by titration according to DIN 53 185.

The refractive index nD20 is determined as the critical angle of total internal reflection of the light of the wavelength of the D-line in the Na emission spectrum (589 nm). The measuring instrument used was an "Automatic Refractometer GPR 11-37" from Index Instruments.

Mol-% data were determined by NMR spectroscopy and, unless indicated otherwise, always relate to the sum of the NCO secondary products. The measurements were carried out using DPX 400 or DRX 700 instruments from Brucker on approximately 5% (1H-NMR) or approximately 50% (13C-NMR) samples in dry C6D6 at a frequency of 400 or 700 MHz (1H-NMR) or 100 or 176 MHz (13C-NMR). As reference for the ppm scale there were used small amounts of tetramethylsilane in the solvent with 0 ppm 1H-NMR chem. shift. Alternatively, the signal of the C6D5H contained in the solvent was used as reference: 7.15 ppm $^1$H-NMR chem. shift, 128.02 ppm $^{13}$C-NMR chem. shift. Data for the chemical shift of the compounds in question were taken from the literature (see D. Wendisch, H. Reiff and D. Dieterich, Die Angewandte Makromolekulare Chemie 141, 1986, 173-183 and literature cited therein, as well as EP-A 896 009).

The residual monomer contents were determined by gas chromatography.

Unless indicated otherwise, all the reactions were carried out under a nitrogen atmosphere.

The diisocyanates used are products of Bayer MaterialScience AG, D-51368 Leverkusen; all other commercially available chemicals were obtained from Aldrich, D-82018 Taufkirchen. The preparation of the hydrogen polyfluoride catalysts is known in the literature and is described inter alia in EP 962 454.

Example 1 Comparative Example 1000 g of HDI were placed in a double-walled flat ground flange vessel adjusted to 40° C. by an external circuit and having a stirrer, a reflux condenser connected to an inert gas system (nitrogen/vacuum) and a thermometer, and freed of dissolved gases by stirring for one hour in vacuo (0.1 mbar). After aeration with nitrogen, the refractive index at the frequency of the light of the D-line of the Na emission spectrum was measured at 20° C. ($n_D^{20}$ hereinbelow), heating to the minimum temperature indicated in Table 1 was carried out, and then the amount of catalyst indicated in Table 1 (based on the mass of HDI used, in the form of a 70% solution in isopropanol) was metered in in portions in such a manner that the internal temperature did not exceed the maximum value indicated in Table 1. When about 1 mol of NCO groups had been converted, the catalyst was deactivated by addition of an amount of p-toluenesulfonic acid (in the form of a 40% solution in isopropanol) equivalent to the catalyst, and the mixture was then stirred for a further 30 minutes at reaction temperature and subsequently worked up.

Working up of the crude solution, the $n_D^{20}$ of which was 1.4618 in the first pass (Example 1-A), was carried out by vacuum distillation in a thin-film evaporator, short path evaporator (SPE) type, with an upstream pre-evaporator (PE) (distillation conditions: pressure: 0.08+/−0.04 mbar, PE temperature: 120° C., SPE temp.: 140° C.), unconverted monomer being separated off as the distillate and the low-monomer polyisocyanate resin being separated off as the bottom product (initial pass: Example 1-A). The polyisocyanate resin was separated off and the distillate was collected in a second flat ground flange stirring apparatus, of identical construction to the first, and made up to the starting amount (1000 g) with freshly degassed HDI. The procedure was then as described at the beginning, with the difference that the isocyanate conversion (indicated by the refractive index of the raw materials) and/or the reaction temperature was raised stepwise from pass to pass. This procedure was repeated several times. The results are to be found in Table 1.

TABLE 1

| Ex. 1- | Reaction temperature (min-max) [° C.] | $Bu_4P^+[HF_2]^-$ solution[a] [g] | Delta-$n_D^{20}$ [b] | Amount of resin [g] | Resin NCO content [%] | Iminooxadiazinediones[c] | Isocyanurates[c] | Uretdiones[c] |
|---|---|---|---|---|---|---|---|---|
| A | 40-42 | 0.83 | 0.0093 | 191 | 23.6 | 41.0% | 57.9% | 1.1% |
| B | 60-62 | 0.35 | 0.0081 | 207 | 23.0 | 44.0% | 53.0% | 3.0% |
| C | 80-84 | 0.49 | 0.0075 | 156 | 23.9 | 27.0% | 67.5% | 5.5% |
| D | 100-105 | 1.14 | 0.0065 | 165 | 23.8 | 26.2% | 57.9% | 15.9% |
| E | 60-62 | 0.40 | 0.0122 | 251 | 23.7 | 43.0% | 51.0% | 6.0% |
| F | 80-81 | 0.36 | 0.0135 | 252 | 23.1 | 31.3% | 58.9% | 9.8% |
| G | 100-105 | 1.86 | 0.0134 | 284 | 22.8 | 23.4% | 69.2% | 7.4% |
| H | 60-62 | 0.71 | 0.0191 | 385 | 22.4 | 42.9% | 53.9% | 3.2% |
| I | 80-81 | 0.78 | 0.0189 | 358 | 22.3 | 28.9% | 63.7% | 7.4% |
| J | 100-105 | 5.20 | 0.0176 | 398 | 22.0 | 14.4% | 71.0% | 14.6% |
| K | 60-62 | 0.80 | 0.028 | 535 | 21.0 | 38.2% | 58.3% | 3.5% |
| L | 80-81 | 1.07 | 0.0292 | 508 | 20.8 | 24.4% | 70.8% | 4.7% |
| M | 60-62 | 1.12 | 0.0327 | 608 | 20.5 | 37.7% | 60.0% | 2.3% |
| N | 60-62 | 1.18 | 0.0395 | 696 | 19.2 | 32.5% | 65.8% | 1.7% |
| O | 60-62 | 1.20 | 0.0484 | 804 | 17.5 | 32.0% | 65.7% | 2.3% |

[a] 70% in iPrOH;
[b] Refractive index of the reaction mixture after action of the stopper before distillation-starting value before catalyst addition,
[c] mol-% acc. to NMR, based on the sum of the stated 3 NCO secondary products formed in the modification reaction, not taken into consideration: urethanes/allophanates from the reaction of the catalyst solvent with the isocyanate Example 2 According to the Invention Additive: 5% Succinonitrile The procedure was as described in Example 1, with the difference that 5% succinonitrile was added once to the degassed HDI before the first reaction (Example 2-A). The reaction temperature was between 60 and 62° C. The results are to be found in Table 2.

TABLE 2

| Ex. 2 | $Bu_4P^+[HF_2]^-$ solution[a] [g] | Delta-$n_D$[b] | Amount of resin [g] | Resin-NCO [%] | Iminooxadiazinediones[c] | Isocyanurates[c] | Uretdiones[c] |
|---|---|---|---|---|---|---|---|
| A | 1.83 | 0.0070 | 180 | 23.4 | 67.0% | 29.1% | 3.9% |
| B | 1.83 | 0.0064 | 173 | 23.4 | 63.8% | 31.9% | 4.3% |
| C | 1.84 | 0.0069 | 169 | 23.3 | 60.6% | 35.4% | 4.0% |

TABLE 2-continued

| Ex. 2 | Bu$_4$P$^+$[HF$_2$]$^-$ solution[a] [g] | Delta-n$_D$[b] | Amount of resin [g] | Resin-NCO [%] | Iminooxa-diazinediones[c] | Iso-cyanurates[c] | Uret-diones[c] |
|---|---|---|---|---|---|---|---|
| D | 1.88 | 0.0072 | 172 | 23.3 | 62.1% | 33.9% | 4.0% |
| E | 2.06 | 0.0069 | 171 | 23.3 | 61.5% | 34.4% | 4.1% |

[a]-[c] see footnotes to Table 1

Example 3 According to the Invention

Additive: 1% Succinonitrile, Variation of the Reaction Temperature and of the Conversion The procedure was as described in Example 1, with the difference that 1% succinonitrile was added once to the degassed HDI before the first reaction (Example 3-A). The further reaction parameters and results are to be found in Table 3.

TABLE 3

| Ex. 3- | Reaction temperature [° C.], +/-0.5° C. | Bu$_4$P$^+$[HF$_2$]$^-$ solution[a] [g] | Delta-n$_D^{20}$[c] | Amount of resin [g] | Resin NCO content [%] | Iminooxa-diazinediones[d] | Iso-cyanurates[d] | Uretdiones[d] |
|---|---|---|---|---|---|---|---|---|
| A | 60 | 1.77 | 0.0090 | 174 | 23.5 | 62.1% | 33.8% | 4.1% |
| B | 60 | 1.49 | 0.0100 | 194 | 23.5 | 63.6% | 32.7% | 3.8% |
| C | 60 | 1.40 | 0.0100 | 198 | 23.6 | 64.2% | 31.7% | 4.1% |
| D | 40 | 0.83 | 0.0095 | 191 | 23.6 | 47.6% | 50.8% | 1.6% |
| E | 80 | 2.03 | 0.0088 | 169 | 23.4 | 55.2% | 35.7% | 9.1% |
| F | 100 | 2.80 | 0.0084 | 171 | 23.2 | 36.9% | 45.7% | 17.3% |
| G | 60 | 1.21 | 0.0135 | 274 | 22.8 | 60.1% | 36.1% | 3.8% |
| H | 80 | 2.50 | 0.0131 | 265 | 23.0 | 52.7% | 38.6% | 8.7% |
| I | 60 | 2.41 | 0.0203 | 384 | 22.3 | 61.9% | 34.3% | 3.8% |
| J | 80 | 2.78 | 0.0191 | 364 | 22.1 | 48.4% | 44.7% | 6.9% |
| K | 60 | 2.57 | 0.0237 | 515 | 20.9 | 60.5% | 36.5% | 3.0% |
| L | 80 | 4.09 | 0.0294 | 493 | 20.8 | 44.9% | 50.2% | 4.9% |

[a]-[c] see footnotes to Table 1

As is apparent from a comparison of the corresponding experiments from comparative example 1 and the results listed in Table 3, the addition of succinonitrile has a positive effect with regard to the maintenance of as high an iminooxadiazinedione group content in the products as possible both when the monomer conversion is increased (higher amount of resin) and when the reaction temperature is increased.

Example 4 According to the Invention

Catalyst Solution with Additive

The procedure was as described in Example 1, with the difference that 12.3% succinonitrile was added to the catalyst solution in the first 6 tests of the series (approximately equimolar based on catalyst). The reaction temperature was between 60 and 65° C. The results are to be found in Table 4.

TABLE 4

| Ex. 4 | Bu$_4$P$^+$[HF$_2$]$^-$ solution[a] [g] | Delta-n$_D$[b] | Amount of resin [g] | Resin-NCO [%] | Iminooxa-diazinediones[c] | Iso-cyanurates[c] | Uretdiones[c] |
|---|---|---|---|---|---|---|---|
| A | 0.79 | 0.0090 | 176 | 23.7 | 49.0% | 46.5% | 4.5% |
| B | 0.69 | 0.0078 | 175 | 23.4 | 47.6% | 49.0% | 3.4% |
| C | 0.73 | 0.0110 | 216 | 23.6 | 53.5% | 41.6% | 4.9% |
| D | 0.66 | 0.0078 | 170 | 23.7 | 56.7% | 38.7% | 4.5% |
| E | 0.53 | 0.0077 | 172 | 23.3 | 59.8% | 36.5% | 3.6% |
| F | 0.63 | 0.0074 | 172 | 23.6 | 58.4% | 36.6% | 5.0% |
| G | 0.69 | 0.0090 | 174 | 23.7 | 57.4% | 37.2% | 5.5% |
| H | 0.56 | 0.0085 | 174 | 23.6 | 56.1% | 38.7% | 5.2% |
| I | 0.51 | 0.0074 | 162 | 23.4 | 58.0% | 37.0% | 5.0% |
| J | 0.53 | 0.0076 | 170 | 23.6 | 58.1% | 37.1% | 4.8% |
| K | 0.54 | 0.0082 | 172 | 23.5 | 58.1% | 37.1% | 4.7% |

[a] to test 4-F approx. 60% in iPrOH, comprises 12.3% succinonitrile, from test 4-G 70% in iPrOH;
[b])-[c] see footnotes to Table 1

The results show that the use of succinonitrile as an additive in the catalysed production of polyisocyanates comprising iminooxadiazinedione groups brings about a significant increase in the iminooxadiazinedione content in the products.

In addition, the examples show that the selectivity of the reaction in respect of the iminooxadiazinedione formation is less strongly dependent on the reaction temperature than in the case of the processes known hitherto.

The invention claimed is:

1. A method for producing polyisocyanates containing iminooxadiazinedione groups, wherein the method comprises oligomerizing at least one monomeric di- and/or tri-isocyanate in the presence of at least one catalyst and succinonitrile, wherein the catalyst is a tetraorganyl-ammonium salt or a tetraorganyl-phosphonium salt, wherein the anions of the tetraorganyl-ammonium salt or tetraorganyl-phosphonium salt are selected from the group: $RfCR_1R_2COO^-$, wherein Rf represents a straight-chained or branched perfluoroalkyl radical and $R_1$ and $R_2$ independently represent H, straight-chained or branched organyl radicals, fluoride ($F^-$), di- and/or poly-(hydrogen) fluorides ($[F^- \times HF)_m]$), and wherein m has a numerical value of from 0.001 to 20.

2. The method according to claim 1, wherein the amount of succinonitrile is from 0.001 to 30%, based on the monomeric di- and/or tri-isocyanate.

3. The method according to claim 1 wherein the monomeric di- and/or tri-isocyanate comprises an aliphatic diisocyanate.

4. The method according to claim 1, wherein the di- and/or poly-(hydrogen) fluoride ($[F^- \times HF)_m]$) is selected from the group consisting of a quaternary ammonium fluoride, ammonium difluoride, ammonium trifluoride, an ammonium polyfluoride, a phosphonium fluoride, a phosphonium difluoride, a phosphonium trifluoride and/or a phosphonium polyfluoride.

5. The method according to claim 1, wherein the catalyst is used in an amount of from 1 mol-ppm to 1 mol-%, based on the amount of monomeric di- and/or tri-isocyanate.

6. The method according to claim 1, wherein the method is carried out in the temperature range of from 0° C. to +250° C.

7. The method according to claim 1, wherein the oligomerization is terminated when from 5 to 80 wt. % of the monomeric di- and/or tri-isocyanate used has been converted.

8. The method according to claim 7, wherein the oligomerization is terminated by deactivation of the catalyst.

9. The method according to one of claims 7 and 8, characterised wherein unconverted monomer is separated from the reaction mixture.

10. The method according to claim 2, wherein that the amount of succinonitrile is from 0.001 to 10%.

11. The method according to claim 2, wherein that the amount of succinonitrile is from 0.01 to 5%.

12. The method according to claim 3, wherein the aliphatic diisocyanate is selected from the group consisting of hexamethylene diisocyanate (HDI), 2-methylpentane 1,5-diisocyanate, 2,4,4-trimethyl-1,6-hexane diisocyanate, 2,2,4-trimethyl-1,6-hexane diisocyanate and/or 4-isocyanatomethyl-1,8-octane diisocyanate.

13. The method according to claim 3, wherein the aliphatic diisocyanate is hexamethylene diisocyanate (HDI).

14. The method according to claim 5, wherein the catalyst is included in an amount of from 5 mol-ppm to 0.1 mol-%, based on the amount of monomeric di- and/or tri-isocyanate.

15. The method according to claim 6, wherein the method is carried out in the temperature range of from 20 to 180° C.

16. The method according to claim 1, wherein the method is carried out in the temperature range of from 40 to 150° C.

17. The method according to claim 1, wherein the method is carried out in the temperature range of from 50 to 90° C.

18. The method according to claim 1, wherein the oligomerization is terminated when from 10 to 60 wt. % of the monomeric di- and/or tri-isocyanate used has been converted.

19. The method according to claim 8, wherein the deactivation occurs by one or more members selected from the group consisting of addition of an acid or of a derivative thereof, an acid ester of acids containing phosphorus or sulfur, an acid containing phosphorus or sulfur, adsorptive binding of the catalyst and subsequent separation by filtration, or combinations thereof.

20. The method according to claim 5, wherein the catalyst comprises a catalyst mixture.

21. The method according to claim 14, wherein the catalyst comprises a catalyst mixture.

22. A reaction system for producing polyisocyanates containing iminooxadiazinedione groups, the reaction system comprising at least one monomeric di- and/or tri-isocyanate at least one catalyst and succinonitrile, wherein the catalyst is a tetraorganyl-ammonium salt or a tetraorganyl-phosphonium salt, wherein the anions of the tetraorganyl-ammonium salt or tetraorganyl-phosphonium salt are selected from the group: $RfCR_1R_2COO^-$, wherein Rf represents a straight-chained or branched perfluoroalkyl radical and $R_1$ and $R_2$ independently represent H, straight-chained or branched organyl radicals, fluoride ($F^-$), di- and/or poly-(hydrogen) fluorides ($[F^- \times HF)_m]$), and wherein m has a numerical value of from 0.001 to 20.

* * * * *

UNITED STATES PATENT AND TRADEMARK OFFICE
CERTIFICATE OF CORRECTION

PATENT NO. : 9,938,369 B2
APPLICATION NO. : 14/905853
DATED : April 10, 2018
INVENTOR(S) : Frank Richter and Reinhard Halpaap Page 1 of 1

It is certified that error appears in the above-identified patent and that said Letters Patent is hereby corrected as shown below:

On the Title Page

Item (72), delete the name:
"Reinhard Halpasp"

And insert therefor:
-- Reinhard Halpaap --

Signed and Sealed this
Fourteenth Day of August, 2018

Andrei Iancu
*Director of the United States Patent and Trademark Office*